United States Patent [19]

Cioca et al.

[11] 4,285,986

[45] Aug. 25, 1981

[54] OLIGOPEPTIDES DERIVED FROM COLLAGEN

[75] Inventors: Gheorghe Cioca, Belleview; Marcel Siegler, North Bergen, both of N.J.

[73] Assignee: Seton Company, Newark, N.J.

[21] Appl. No.: 113,694

[22] Filed: Jan. 21, 1980

[51] Int. Cl.$^3$ ................................................. A23J 1/10
[52] U.S. Cl. ................................. 426/657; 260/123.7; 426/429; 426/431; 426/437
[58] Field of Search .................... 206/123.7; 426/657, 426/431, 437, 429

[56] References Cited

U.S. PATENT DOCUMENTS

| | | | |
|---|---|---|---|
| 3,322,632 | 5/1967 | Schwick et al. | 424/92 X |
| 3,743,514 | 7/1973 | Olson et al. | 260/123.7 UX |
| 4,100,154 | 7/1978 | Holloway | 260/123.7 |

*Primary Examiner*—Howard E. Schain

[57] ABSTRACT

A method of preparing oligopeptides from collagen is disclosed. Collagen containing material is treated with an aqueous solution of a member selected from the group consisting of an alkali earth metal hydroxide, an alkali metal hydroxide and mixtures thereof in the presence of an agent which prevents overswelling of the collagen. The treatment removes substantially all of the hair and fat from the collagen. The remaining non-collagenous material is removed by treating the dehaired and defatted collagen with an aqueous solution which acts as a solvent for the non-collagenous material. The collagen is neutralized and residual salts are removed therefrom. The collagen is heated under pressure in the presence of water to hydrolyze polypeptide chains to form oligopeptides having a molecular weight of between about 5,000 and 20,000. The recovered oligopeptides are particularly useful as a trophic agent for feeding animals.

7 Claims, No Drawings

OLIGOPEPTIDES DERIVED FROM COLLAGEN

BACKGROUND OF THE INVENTION

This invention relates to collagen and more particularly to oligopeptides derived from collagen.

"Natural insoluble collagen" as used herein means and refers to collagen which cannot be dissolved in an aqueous alkaline or in any inorganic salt solution without chemical modification and includes hides, splits, and other mammillian or reptilian coverings. More particularly, "natural insoluble collagen" means and refers to the corium which is the intermediate layer of a bovine hide between the grain and the flesh sides.

Collagen constitutes the connective tissue and is the major type of fibrous protein in higher vertebrae. Collagen in its natural state exists in a triple chain helix along with a constant periodicity between aligned triple chains. The triple helical configuration of collagen is sometimes referred to as a fibril and the fibrils align with an axial periodicity of about 640 Å.

Although there are several types of collagen, the major type is referred to as "type I" which is the major collagen of skin, bones and tendons. The type I collagen has a chain composition of $[\alpha 1(I)_2 \alpha 2]$. The $\alpha 1(I)$ and $\alpha 2$ chains are homologous.

In young animals there is little intermolecular and interfibrilar crosslinking which provides for some degree of solubility of the collagen. However, during the aging process both intermolecular and interfibrilar crosslinking occurs, thus making the collagen insoluble.

The collagen and related materials have found utility in the food, cosmetic and pharmaceutical fields. More particularly, in the nutritional field it is known that protein which has been enzymatically digested can be used for nutritive purposes; however, the residual enzymes in the predigest have various undesirable effects.

Further, it is known to sever collagen chains into oligopeptides by treating the collagen with strong base; however, the oligopeptides produced are somewhat impure and are not particularly adapted for food purposes.

In accordance with the present invention a process for preparing oligopeptides from collagen is provided which removes substantially all the impurities therefrom and does not require enzymatic digestion.

BRIEF DESCRIPTION OF THE INVENTION

A method of preparing oligopeptides from collagen is disclosed. Collagen containing material is treated with an aqueous solution of a member selected from the group consisting of an alkali earth metal hydroxide, an alkali metal hydroxide and mixtures thereof in the presence of an agent which prevents overswelling of the collagen. The treatment removes substantially all of the hair and fat from the collagen. The remaining non-collagenous material is removed by treating the dehaired and defatted collagen with an aqueous solution which acts as a solvent for the non-collagenous material. The collagen is neutralized and residual salts are removed therefrom. The collagen is heated under pressure in the presence of water to hydrolyze polypeptide chains to form oligopeptides having a molecular weight of between about 5,000 and 20,000. The recovered oligopeptides are particularly useful as a trophic agent for feeding animals.

DETAILED DESCRIPTION OF THE INVENTION

The collagen containing material may be obtained from a variety of sources well known to those skilled in the art. Preferably, the source of collagen is natural insoluble collagen from a bovine hide.

The alkali metal hydroxides useful in the practice of the invention are sodium and potassium hydroxide, and more preferably, sodium hydroxide. Alkali earth metal hydroxides such as calcium hydroxide and magnesium hydroxide may be substituted in part for the alkali metal hydroxides; however, sufficient potassium and/or sodium hydroxide must be provided to hydrolyze the fats present in the collagen containing material. The alkali earth metal hydroxides useful in the practice of the invention are required to dehair the hide.

The agent which prevents the overswelling of the collagen is preferably a salt such as sodium chloride or potassium chloride or an alkali sulfate such as sodium or potassium sulfate or an alkali metal sulfate, preferably sodium chloride or potassium chloride is used. Further, lower alcohols having 1 to 4 carbon atoms may also be used as an agent to prevent overswelling of the collagen. The aqueous solution of the alkali hydroxide, alkali earth metal hydroxide, and an agent which prevents overswelling of the collagen, is composed of 1 molar to 2.5 molar of the combined alkali earth metal hydroxide, 0.5 molar to 1 molar of the agent which prevents overswelling of the collagen, and more preferably, 2.0 molar to 2.5 molar of the combined alkali metal hydroxide and alkali earth metal hydroxide and 0.9 molar to 1.0 molar of the agent to prevent overswelling of the collagen. Other salt constituents may be added at a level of about 0.1 molar to 0.2 molar. The resultant aqueous solution should be at an initial pH of about 12 to 13.

Care should be taken to properly proportion the alkali earth metal hydroxide, the alkali metal hydroxide and the agent to prevent overswelling of the collagen in order to provide for complete saponification of fats suspended within the natural insoluble collagen while retaining the native characteristics of the collagen and controlling the swelling of the collagen fibers. If too much sodium hydroxide is used the collagen will be denatured and intermolecular bonds will be severed solubilizing some of the polypeptide chains thereby lowering the yield of oligopeptides. If insufficient sodium hydroxide is used the collagen product will have retained impurities such as fats and other hydrolyzable materials which are undesirable.

In treating the collagen containing material with the aqueous solution previously described, the collagen containing material should be cut into pieces which are sufficiently small so that aqueous solution may penetrate and react therein. The natural insoluble collagen containing pieces should be about 10 cubic centimeters and more preferably 5 cubic centimeters or less. Treatment in the aqueous solution should be for about 1 to 7 days to dehair and defat the collagen containing material. The collagen containing material substantially free of hair and fat is delimed and neutralized to a pH of about 7 by treating with an acidic buffer solution having a pH of 2 to 3.5, for example, the combination of ammonium chloride and hydrochloric acid may be used for the deliming and acidification. The pH of the cross section of the collagen containing material after extraction should be about 7. The neutralized collagen containing material is preferably washed with running water and deposited in distilled water overnight, i.e. from about 8 to 12 hours, to extract any residual salts or soluble impurities retained in the material.

The water is removed and the collagen is treated under heat and pressure for 6 to 15 hours at a pressure of 1 to 2.5 atmospheres at a temperature of 120° C. to 150° C. Sufficient water is retained within the collagen to effect hydrolysis under these conditions. This hydrolysis treatment hydrolyzes various polypeptide bonds to produce the oligopeptides which are the desired product. Typically these oligopeptides have a molecular weight of between 5,000 and 20,000.

After hydrolysis under heat and pressure, the oligopeptides, in aqueous media, are cooled to about preferably 4° C. The fats solidify and float to the top and other impurities sediment to the bottom. The oligopeptides are soluble in the aqueous phase of the media. The sediment is removed and fat is skimmed from the surface thereof and what is remaining is a solution having 10 to 15 percent solids containing substantially pure collagen oligopeptides.

The solution containing the oligopeptides can then be spray dried or dried by other conventional techniques to form a dry stable powder.

One particularly useful application of the collagen oligopeptides is in combining the oligopeptides with various micronutrients to be used in the feeding of suckling pigs during the weaning stage. Typical micronutrients are ascorbic acid, calcium phosphate, salt, sodium chloride, vitamin A, vitamin $D_3$, vitamin $B_1$, vitamin $B_2$, vitamin $B_6$, vitamin $B_{12}$, vitamin PP, vitamin K, pantothenic acid, choline chloride, cobalt, iron, iodine, manganese, copper and zinc. In addition to the micronutrients other bulk nutrients may be added such as sugars, for example, glucose, sucrose, fructose, maltose and the like. It has been found that the oligopeptides complex with the bulk nutrients and micronutrients. Upon digestion by pigs in the weaning stage, the oligopeptides effect placing the micronutrients and bulk nutrients into the system of the animal. The use of the oligopeptides in connection with the bulk and micronutrients provides for reduced mortality of pigs during the weaning stage and provides an increased utilization of food by way of weight gain and health.

In combining the collagen oligopeptides with the micronutrients, the oligopeptides in solution form are mixed with the particular micronutrients desired. The mixture of micronutrients with the oligopeptide solution is heated at a sufficient temperature for a sufficient time to complex the micronutrients with the oligopeptides. Preferably, the heating is conducted at a temperature of 50°–100° C. for one to five hours. Subsequent to heating, the admixture is concentrated by vacuum distillation or the like to 20 to 35 percent solids and spray dried through conventional spray drying equipment. The micronutrients complexed with the oligopeptides can be used as is, or added to bulk animal food in a percentage range of 10 to 50 percent.

The invention will be further understood by reference to the following examples.

EXAMPLE 1

One hundred kilograms of collagen containing material including raw hide, untanned tannery wastes, lime splits and trimming scraps are charged to a suitable vessel containing 300 liters of water having therein 10 kg of calcium hydroxide and 5 kg of sodium hydroxide and 5 kg of sodium chloride. The collagen containing materials are allowed to stand in the aqueous solution for five days. After five days the vessel is drained and the collagen containing material free of hair and fats are neutralized to a pH of 7 by treating with an aqueous solution of 30 liters water which contains 1.5 kg of ammonium chloride and 1.5 kg of hydrochloric acid. The pH of the cross section of the collagen is about 7. The neutralized collagen is washed with 300 liters of running water and deposited in 600 liters of distilled water for 12 hours. The distilled water extracts residual salts from the collagen. The distilled water is drained and the collagen is charged to an autoclave for eight hours at a pressure of 2 $kg/cm^2$. The treatment under heat and pressure hydrolyzes the polypeptide bonds and the collagen is hydrolyzed to form oligopeptides having a molecular weight between 5,000 and 20,000. After treatment under heat and pressure, the oligopeptide solution is cooled to about 4° C. and a small amount of fat rises to the surface of the solution and minor impurities precipitate. The collagen oligopeptides are then heated and filtered through filter paper and mixed with 3 percent activated charcoal to remove any residual impurities and the oligopeptide solution is filtered through filter paper.

EXAMPLE 2

One hundred liters of collagen oligopeptide solution prepared in accordance with Example 1 at about 15 percent solids is charged to a suitable vessel along with 5 kg of glucose, 0.5 kg of sodium chloride, 0.2 kg of calcium phosphate, 0.1 kg of ferric chloride, 0.01 kg of calcium diphosphate and 0.1 kg of ascorbic acid. The admixture is heated to 100° C. for three hours and subsequent to heating is concentrated by evaporation of the water to 20 to 35 percent solids and spray dried on a conventional spray drying apparatus with an entrance temperature of 150° C. and an exit temperature of 80° C.

The product in accordance with Example 2 can be fed directly to animals such as sucklings pigs, or can be added to animal feed in a percentage of 10 to 50 percent by weight.

EXAMPLE 3

Example 2 was repeated except the nutrients added were 0.01 kg of ascorbic acid, 0.1 kg of calcium phosphate, 0.1 kg of potassium chloride, 0.2 kg of calcium diphosphate, 0.5 kg of sodium chloride, and additionally 5 kg of glucose and 50 liters of keratin hydrolysate having 15 percent solids.

EXAMPLE 4

Example 2 is repeated except that 1 to 5 grams of iodine as a disinfectant is added to the collagen oligopeptide-micronutrient combination. The iodine is added as a 10 percent solution in ethyl alcohol.

The combination of collagen oligopeptides and micronutrients is found to be effective in feeding pigs during the weaning stage and reduces the mortality rate in the suckling pigs, and further, enhances the nutritive characteristics of food used in combination therewith.

Thus, although the invention has been described with reference to specific materials and specific process conditions, the invention is only to be limited so far as is set forth in the accompanying claims.

We claim:
1. A method of preparing oligopeptides from collagen comprising:

treating natural insoluble collagen with an aqueous solution of a member selected from the group consisting of a mixture of an alkali earth metal hydroxide and an alkali metal hydroxide; and an alkali metal hydroxide in the presence of an agent which prevents overswelling of the collagen, said treatment removing substantially all of the hair and fat from the collagen;

removing non-collagenous material by treating the dehaired and defatted collagen with an aqueous solution of a solvent for said non-collagenous material;

neutralizing the collagen;

removing residual salts from said collagen;

heating the collagen under pressure in the presence of water to hydrolyze polypeptide chains to form oligopeptides; and recovering substantially pure oligopeptides having a molecular weight between about 5,000 and 20,000.

2. The method of claim 1 wherein the alkali metal hydroxide and alkali earth metal hydroxide are present at a level of 1 molar to 2.5 molar.

3. The method of claim 1 wherein said agent which prevents the overswelling of the collagen is a salt.

4. The method of claim 3 wherein the agent which prevents the overswelling of the collagen is sodium chloride.

5. The method of claim 1 wherein the collagen is heated under a pressure of 1 to 2.5 atmospheres at a temperature of 120° C. to 150° C. to hydrolyze the polypeptide chains to form oligopeptides.

6. The oligopeptides prepared in accordance with claim 1.

7. A trophic agent comprising:
oligopeptides prepared in accordance with claim 1 and micronutrients.

* * * * *

UNITED STATES PATENT AND TRADEMARK OFFICE
CERTIFICATE OF CORRECTION

PATENT NO. : 4,285,986
DATED : August 25, 1981
INVENTOR(S) : Gheorghe Cioca and Marcel Siegler It is certified that error appears in the above-identified patent and that said Letters Patent are hereby corrected as shown below:

Column 2 Line 28 Delete the comma "," and insert

--and alkali metal hydroxide,--.

Signed and Sealed this

Twenty-seventh Day of October 1981

[SEAL]

Attest:

GERALD J. MOSSINGHOFF

Attesting Officer     Commissioner of Patents and Trademarks